US00PP17928P2

(12) United States Plant Patent
van Leeuwen

(10) Patent No.: US PP17,928 P2
(45) Date of Patent: Aug. 21, 2007

(54) *DIANTHUS* PLANT NAMED 'WESNAVI'

(50) Latin Name: *Dianthus caryophyllus*
Varietal Denomination: Wesnavi

(75) Inventor: Gijsbertus van Leeuwen, 's-Gravenzande (NL)

(73) Assignee: West Select B.V., 's-Gravenzande (NL)

( * ) Notice: Subject to any disclaimer, the term of this patent is extended or adjusted under 35 U.S.C. 154(b) by 0 days.

(21) Appl. No.: 11/323,159

(22) Filed: Dec. 30, 2005

(51) Int. Cl.
*A01H 5/00* (2006.01)

(52) U.S. Cl. ..... Plt./272
(58) Field of Classification Search ..... Plt./272, Plt./273
See application file for complete search history.

(56) References Cited

PUBLICATIONS

GTITM UPOVROM Citation for 'WesnavI' as per QZ PBR 20031696; Sep. 24, 2003.*

GTITM UPOVROM Citation for 'WesnavI' as per QZ PBR 20041853; Oct. 4, 2004.*

* cited by examiner

*Primary Examiner*—Kent Bell
(74) *Attorney, Agent, or Firm*—C. A. Whealy

(57) ABSTRACT

A new and distinct cultivar of *Dianthus* plant named 'Wesnavi', characterized by its large white-colored flowers with red-colored picotee petal margins and random spots and streaks; good postproduction longevity with flowers maintaining good substance and color for about two days as a cut flower; and resistance to *Fusarium oxysporum*.

1 Drawing Sheet

Botanical designation: *Dianthus caryophyllus*.
Cultivar denomination: 'Wesnavi'.

BACKGROUND OF THE INVENTION

The present invention relates to a new and distinct cultivar of potted *Dianthus* plant, botanically known as *Dianthus caryophyllus* and hereinafter referred to by the name 'Wesnavi'.

The new cultivar is a product of a planned breeding program conducted by the Inventor in 's-Gravenzande, The Netherlands. The objective of the breeding program is to create new cut flower *Dianthus* cultivars having strong stems, larger flowers and attractive flower coloration.

The new *Dianthus* originated from a cross-pollination made by the Inventor in 's-Gravenzande, The Netherlands, of a proprietary selection of *Dianthus caryophyllus* identified as code number WS 99-1077, not patented, as the female, or seed, parent with a proprietary selection of *Dianthus caryophyllus* identified as code number WS 98-843, not patented, as the male, or pollen, parent. The new *Dianthus* was discovered and selected by the Inventor as a single flowering plant within the progeny of the stated cross-pollination grown in a controlled environment in 's-Gravenzande, The Netherlands in July, 2000.

Asexual reproduction of the new *Dianthus* by cuttings propagated in a controlled environment in 's-Gravenzande, The Netherlands, since August, 2001, has shown that the unique features of this new *Dianthus* are stable and reproduced true to type in successive generations.

SUMMARY OF THE INVENTION

The cultivar Wesnavi has not been observed under all possible environmental conditions. The phenotype may vary somewhat with variations in environment such as temperature and light intensity without, however, any variance in genotype.

The following traits have been repeatedly observed and are determined to be the unique characteristics of 'Wesnavi'. These characteristics in combination distinguish 'Wesnavi' as a new and distinct cultivar:

1. Large white-colored flowers with red-colored picotee petal margins and random spots and streaks.
2. Good postproduction longevity with flowers maintaining good substance and color for about two days as a cut flower.
3. Resistant to *Fusarium oxysporum*.

Compared to plants of the female parent selection, plants of the new *Dianthus* have longer and stronger flowering stems and differ in flower color as plants of the female parent selection have dark red-colored flowers. Compared to plants of the male present selection, plants of the new *Dianthus* have stronger flowering stems and differ in flower color as plants of the male parent selection have red-colored flowers.

Plants of the new *Dianthus* can be compared to plants of the cultivar Lando, not patented. In side-by-side comparisons conducted in 's-Gravenzande, The Netherlands, plants of the new *Dianthus* and the cultivar Lando differed in the following characteristics:

1. Plants of the new *Dianthus* had longer, thicker and stronger flowering stems than plants of the cultivar Lando.
2. Plants of the new *Dianthus* had longer internodes than plants of the cultivar Lando.
3. Plants of the new *Dianthus* had longer leaves than plants of the cultivar Lando.
4. Flowers of plants of the new *Dianthus* were white with red-colored picotee petal margins and random spots and streaks whereas flowers of plants of the cultivar Lando were white with dark pink-colored picotee petal margins and random spots and streaks.

5. Plants of the new *Dianthus* were more resistant to *Fusarium oxysporum* than plants of the cultivar Lando.

BRIEF DESCRIPTION OF THE PHOTOGRAPHS

The accompanying colored photographs illustrate the overall appearance of the new *Dianthus,* showing the colors as true as it is reasonably possible to obtain in colored reproductions of this type. Colors in the photographs may differ slightly from the color values cited in the detailed botanical description which accurately describe the colors of the new *Dianthus.*

The photograph at the top of the sheet comprises a side perspective view of a typical flowering stem of 'Wesnavi'.

The photograph at the bottom of the sheet comprises a close-up view of a typical flower of 'Wesnavi'.

DETAILED BOTANICAL DESCRIPTION

In the following description, color references are made to The Royal Horticultural Society Colour Chart, 2001 edition, except where general terms of ordinary dictionary significance are used. The aforementioned photographs, following observations and measurements describe plants grown in 's-Granvenzande, The Netherlands during the spring and summer in a glass-covered greenhouse. During the production of the plants, day temperatures ranged from 15° C. to 25° C. and night temperatures ranged from 10° C. to 16° C. Plants were pinched one time about four weeks after planting. The photographs and the description were taken about eight months after planting.

Botanical classification: *Dianthus caryophyllus* cultivar Wesnavi.

Parentage:

*Female, or seed, parent.*—Proprietary selection of *Dianthus caryophyllus* identified as code number WS 99-1077, not patented.

*Male, or pollen, parent.*—Proprietary selection of *Dianthus caryophyllus* identified as code number WS 98-843, not patented.

Propagation:

*Type.*—By cuttings.

*Time to initiate roots.*—About 20 days at 22° C.

*Time to produce a rooted young plant.*—About 25 days at 22° C.

*Root description.*—Fine, fleshy; white to cream-colored.

*Rooting habit.*—Freely branching.

Plant description:

*Flowering stem description.*—Quantity: After pinching, about nine flowering stems develop per plant. Length: About 80 cm to 90 cm. Diameter: About 5 mm. Internode: About 11 cm. Aspect: Erect. Strength: Very strong. Texture: Smooth, glabrous; waxy. Color: Close to 147A, overlain with waxy bloom, close to 188A.

*Foliage description.*—Arrangement: Opposite; sessile. Aspect: Concave; upright to perpendicular to eventually reflexing. Length: About 15.5 cm. Width: About 9 mm. Shape: Lanceolate. Apex: Sharply acute to acuminate. Base: Clasping. Margin: Entire. Texture, upper and lower surfaces: Tough, leathery; waxy. Venation: Parallel. Color: Developing foliage, upper and lower surfaces: Close to 147A, overlain with waxy bloom, close to 188A. Fully developed foliage, upper and lower surfaces: Close to 147A, overlain with waxy bloom, close to 188A. Venation, upper and lower surfaces: Similar to lamina.

Flowering description:

*Appearance.*—Large single hemispherical flowers; typically grown as a disbud or standard-type with one flower per stem.

*Flowering response.*—Year-round under greenhouse conditions; plants flower about 20 weeks after planting rooted cuttings.

*Postproduction longevity.*—Good postproduction longevity with flowers maintaining good substance and color for about two weeks as a cut flower. Flowers persistent.

*Fragrance.*—Slightly fragrant; spicy, clove-like.

*Flower buds.*—Length: About 1 cm to 1.5 cm. Diameter: About 3 mm to 5 mm. Shape: Oblong. Color: 144A and 173C.

*Flower size.*—Diameter: About 7 cm to 8 cm. Depth (height): About 3 cm to 3.5 cm.

*Petals/petaloids.*—Quantity per flower: About 60, imbricate. Length: About 5 cm to 6 cm. Width: About 3.5 cm to 4 cm. Shape: Roughly spatulate. Apex: Roughly rounded; finely serrated giving a fringed appearance; undulate. Lateral margins: Entire. Texture, upper and lower surfaces: Smooth, glabrous; velvety. Color: When opening and fully opened, upper surface: Close to 155C; towards the margin and random spots and streaks, close to 45D; towards the base, overlain with N144D. When opening and fully opened, lower surface: Close to 155C; towards the margin and random spots and streaks, close to 45D; towards the base, overlain with N144D.

*Sepals.*—Quantity: About six, fused. Length: About 3 cm. Width: About 1.2 cm to 1.5 cm. Calyx length: About 3 cm. Calyx diameter: About 2.5 cm. Shape: Roughly linear. Apex: Apiculate. Texture, upper and lower surfaces: Tough, leathery; smooth; waxy, longitudinally ridged. Color, upper surface: 192C to 192D. Color, lower surface: Close to 146A.

*Reproductive organs.*—Androecium: About ten stamens, mostly transformed into petaloids without developed anthers. Gynoecium: Pistil quantity: About four. Pistil length: About 2.5 cm to 3 cm. Style length: About 1 cm. Style color: Close to 155A. Stigma shape: Linear. Ovary color: Base, close to 155A; mid-section, close to 144B; apex, close to 162A to 162B.

*Seed/fruit.*—Seed and fruit production have not been observed.

Disease/pest resistance: Plants of the new *Dianthus* have been observed to be resistant to *Fusarium oxysporum.* Plants of the new *Dianthus* have not been observed to be resistant to other pathogens and pests common to *Dianthus.*

Temperature tolerance: Plants of the new *Dianthus* have been observed to tolerate temperatures from 0° C. to 35° C.

It is claimed:

1. A new and distinct cultivar of *Dianthus* plant named 'Wesnavi', as illustrated and described.

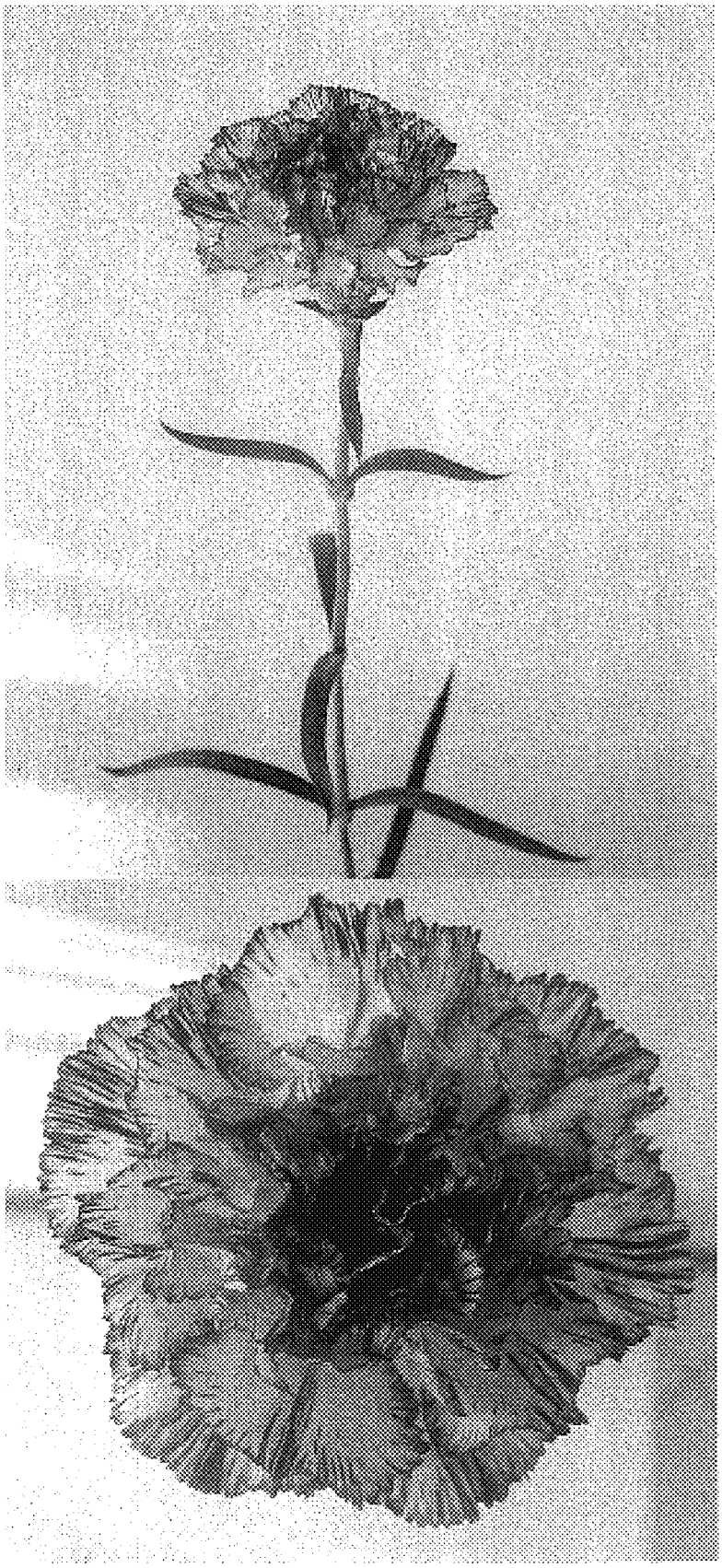

* * * * *